United States Patent [19]

Pelosi, Jr. et al.

[11] 4,202,676
[45] May 13, 1980

[54] SAFETY ENCLOSURE

[76] Inventors: Michael H. Pelosi, Jr.; Raymond Fink, both c/o Airo Clean Engineering, Inc., 520 Abbott Dr., Broomall, Pa. 19008

[21] Appl. No.: 929,834

[22] Filed: Jul. 31, 1978

[51] Int. Cl.² .................... B01D 51/10; A61L 9/00; A61B 19/02
[52] U.S. Cl. .................... 55/269; 55/279; 55/356; 55/385 A; 55/472; 55/482; 55/417; 55/418; 55/502; 55/DIG. 29; 98/115 R; 422/120; 128/1 R
[58] Field of Search ............. 55/269, 279, 356, 385 A, 55/472, 482, 502, DIG. 18, DIG. 29, 417, 418; 98/115 R, 115 LH; 422/4, 120; 128/1 R, 1 B

[56] References Cited

U.S. PATENT DOCUMENTS

| 2,600,501 | 6/1952 | Higgs | 128/1 B |
|---|---|---|---|
| 3,150,584 | 9/1964 | Allander | 55/DIG. 29 |
| 3,158,457 | 11/1964 | Whitefield | 55/482 |
| 3,239,305 | 3/1966 | Potapenko | 55/DIG. 29 |
| 3,272,199 | 9/1966 | Matthews | 128/1 R |
| 3,523,409 | 8/1970 | Paterson | 55/482 |
| 3,777,736 | 12/1973 | van der Warij et al. | 55/385 A |
| 3,828,530 | 8/1974 | Peters | 55/482 |
| 3,841,324 | 10/1974 | Kruiswijk | 55/385 A |
| 3,895,570 | 7/1975 | Eagleson, Jr. | 55/DIG. 19 |

FOREIGN PATENT DOCUMENTS

| 2360153 | 6/1974 | Fed. Rep. of Germany | 98/115 LH |
| 70693 | 2/1944 | Norway | 55/DIG. 29 |

*Primary Examiner*—David L. Lacey
*Attorney, Agent, or Firm*—Zachary T. Wobensmith, 2nd; Zachary T. Wobensmith, III

[57] ABSTRACT

A safety enclosure is disclosed which provides a portable self-contained ultra clean enclosed space environment, with easy access to the interior of the enclosure and which can be operated at relative positive, zero or negative pressure, depending on the usage conditions required so as to provide biological protection for an animal handler or investigator, to reduce contamination of the material inside the enclosure, and to prevent escape of noxious material to the outside.

12 Claims, 5 Drawing Figures

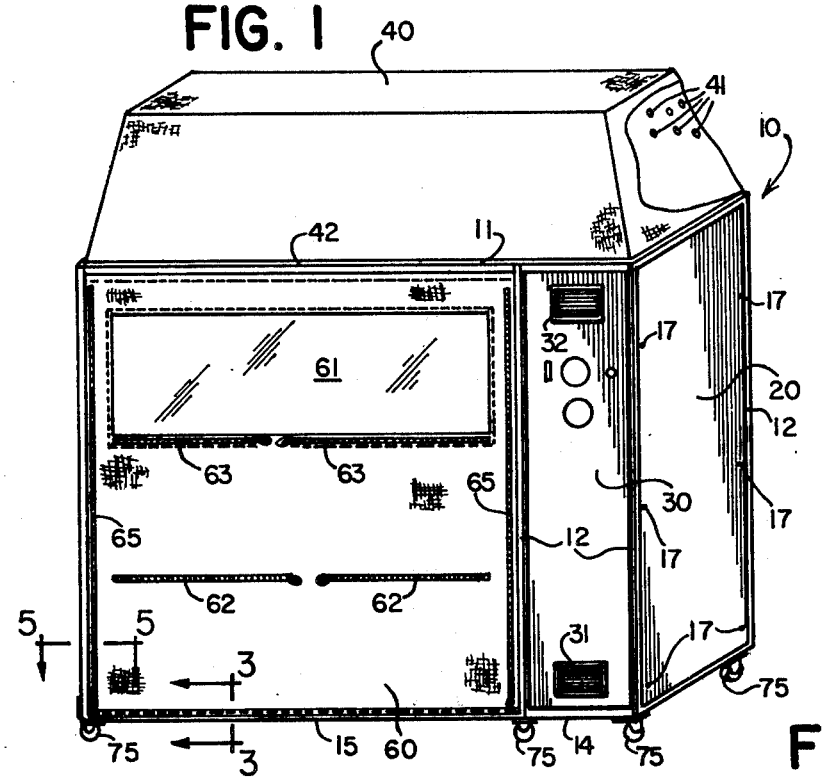
FIG. 1
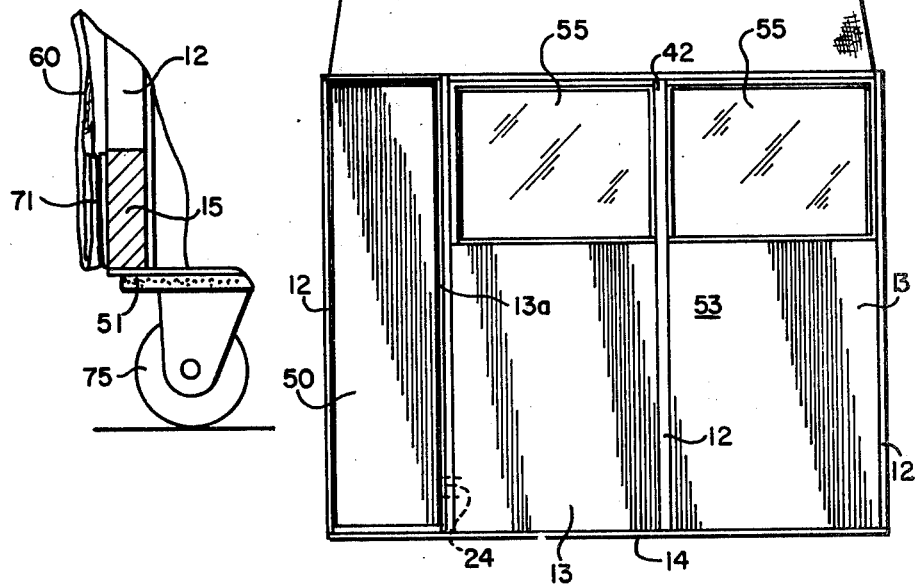
FIG. 3
FIG. 2

SAFETY ENCLOSURE

BACKGROUND OF THE INVENTION

1. Field of the Invention

This invention relates to a portable, self contained safety enclosure which provides a clean space.

2. Description of the Prior Art

The use of portable enclosures to provide a clean room type environment is old in the art, however the previously available structures were usually fixed in place, with limited access to the interior which resulted in limited usefulness of these structures. No protection was available for the operator from infectious bacteria or viruses in animals under test.

The enclosure of the invention is self contained, portable, can be operated at relative positive, zero or negative pressures, provides easy access to the interior, and enjoys other advantages not found in the prior art.

SUMMARY OF THE INVENTION

In accordance with the invention a portable safety enclosure is provided, with an ultra clean room type environment, which is self contained and can be operated at a variety of air pressures to provide safety for the user of animal research, tissue culture and plant life, which has easy access to the enclosure without degradation of the enclosure operation.

The principal object of the invention is to provide a self contained safety enclosure which has a clean room environment and safety enclosure which is portable.

A further object of the invention is to provide a safety enclosure which protects either the user or the subjects being observed from contamination.

A further object of the invention is to provide a safety enclosure which can be operated at positive, zero or negative relative pressures as desired.

Other objects and advantageous features of the invention will be apparent from the description and claims.

BRIEF DESCRIPTION OF THE DRAWINGS

The nature and characteristic features of the invention will be more readily understood from the following description taken in connection with the accompanying drawings forming part hereof in which:

FIG. 1 is a view in perspective of the apparatus of the invention;

FIG. 2 is a rear elevational view of the apparatus of FIG. 1.

FIG. 3 is a fragmentary vertical sectional view, enlarged, taken approximately on the line 3—3 of FIG. 1;

Figure 4:
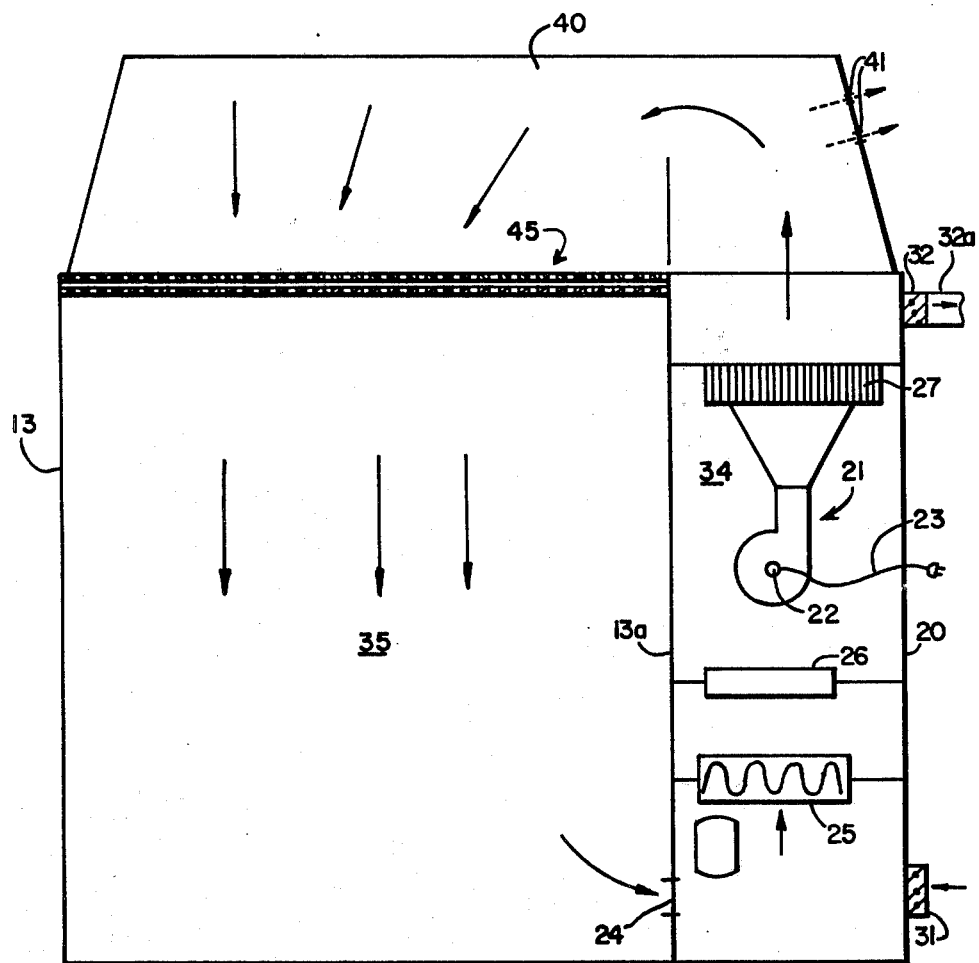
FIG. 4 is a diagrammatic vertical sectional view of FIG. 1.
Figure 5:
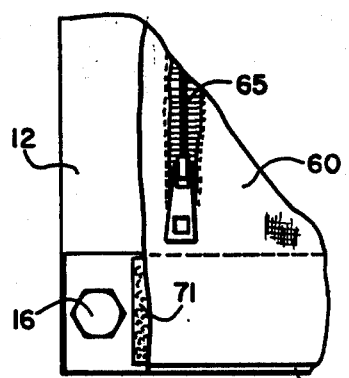
FIG. 5 is a fragmentary vertical sectional view, enlarged, taken approximately on the line 5—5 of FIG. 1.

It should, of course, be understood that the description and drawings herein are illustrative merely and that various modifications and changes can be made in the structure disclosed without departing from the spirit of the invention.

Like numerals refer to like parts throughout the several views.

DESCRIPTION OF THE PREFERRED EMBODIMENTS

Referring now more particularly to the drawings the safety enclosure 10 includes a housing having a supporting frame 11 which is preferably constructed of a plurality of vertical posts 12 and interposed rigid side and rear panels 13, the housing being open at the front but connected at the bottom by a bar 15 removably secured by bolts 16. At the right hand end as seen in FIG. 1 there is provided a metal access panel 20 which is detachably secured to the posts 12 by bolts 17. In a specific embodiment the enclosure frame can be of a height of 72 inches, a width of the order of 92 inches with an interior space of a width of about 70 inches and a depth of the order of 30 inches. The enclosure 10 inside of panel 20 and exteriorly of the contiguous side panel 13a has an air blower 21 of well known type mounted therein with an electric motor 22 which has leads 23 extending therefrom for connection to a source of electrical energy (not shown).

A prefilter 25 can be provided within the enclosure 10 so that air before it enters the blower 21 can be treated and which air can also flow through a cooling or heating coil 26 of well known type interposed between the filter 25 and the blower 21. The blower 21 can be provided with a filter 27 on its discharge side which filter 27 may be of the HEPA type and which has the capability of catching and retaining viruses. A panel 30 is provided at the right front of enclosure 10 closing the front of an air blower chamber 34 which has a variable louvered air inlet 31 at the bottom and a variable air louvered discharge outlet 32 at the top for control of the air pressure within the enclosure 10. The air discharge outlet 32 can, if desired, be provided with a discharge pipe 32a for discharge to the exterior if the air contains gaseous contaminants which might be harmful to the operator. It should be noted that a panel 13a within enclosure 10 is provided which forms the separate chamber 34 within which the air blower 21 and supporting equipment are located and which panel 13a has an air access opening 24 to provide air intake from the operational chamber 35 of the enclosure 10.

The frame 11 at the top thereof is closed off by a deflatable plenum chamber 40 which in the embodiment referred to above has a height of the order of 18 to 21 inches. The plenum chamber 40 is preferably formed of a flexible sheet of synthetic plastic material which is impervious to air. The plenum chamber 40, if desired, and in lieu of the discharge outlet 32, can have a plurality of holes 41 therein in the rear thereof as shown in the FIGS. 1 and 4 to permit controlled escape of air therethrough and thereby provide a continuously negative pressure inside enclosure 10 while still maintaining the chamber 40 in inflated condition.

The plenum chamber 40 is detachably secured to the top of frame 11 and to a cross bar 42 by bolts (not shown).

Below the chamber 40 a perforated double layer ceiling 45 is provided which can be as shown in U.S. Pat. No. 4,060,025 to Michael H. Pelosi, Jr. and is secured to the top of the frame 11 and over the top of the operational chamber 35.

The left hand portion of the frame 11 is closed by a panel 13.

The frame 11 at the bottom thereof may be open with a gasket 51 around the periphery which contacts the floor (not shown) for operation or which may be fitted with a floor (not shown) which is impervious to air and closes off the bottom of frame 11.

The frame 11 is closed at the rear as shown in FIG. 2 by panels 13 and 50 and with a clear window 55 in each of the rear panels 13 affording visibility to the operational chamber 35.

The frame 11 is closed at the front as seen in FIG. 1 by a curtain 60 which is preferably of flexible sheet material impervious to air and which is also carried on the cross bar 42 and side posts 12. The curtain 60 has a clear window 61 therein which can be fabricated of a clear vinyl of well known type and at the bottom thereof is secured to the curtain 60 by a double slider separable fastener 63 which provides access to the operational chamber 35 with minimal air loss. An additional double slider separable fastener 62 is provided between window 61 and the bottom of curtain 60 similar to fastener 63 for additional access to chamber 35.

The curtain 60 at the sides thereof is provided with a separable fastener 65 extending substantially the height of the curtain and providing access into chamber 35 as desired.

The curtain 60 at the bottom has the floor bar 15 extending therealong attached to posts 12 by bolts 16 at each end and to which the curtain 60 is detachably secured by a strip of thistle cloth 71 such as "Velcro". At each corner of the frame 11 casters 75 are provided detachably secured thereto which are utilized to move the enclosure 10 from place to place as desired.

The mode of operation will now be pointed out.

In use the blower 21 is activated and air is discharged into plenum chamber 40 from filter 27 and flows through perforated ceiling 45 into the operational chamber 35 and out at the bottom past a panel (not shown) and back into filter 25 and to blower 21 as described above.

If positive pressure is desired in the chamber 35 then the air discharge outlet 32 is closed and inlet 31 is opened. Access to the operational chamber 35 can be obtained by moving the double slider separable fasteners 62 or 63 without contamination by outside air and with little loss of interior air.

If negative pressure is desired then the air discharge outlet 32 is opened and inlet 31 is closed.

In addition, if continuously negative pressure is desired then the plenum chamber 40 with holes 41 for escape of a controlled amount of air may be provided. The negative pressure operation results in no escape of material outside of the chamber 35 due to the operator's using the fasteners 62 or 63 for access into chamber 35.

If zero pressure is desired the inlet 31 and the air discharge outlet 32 are opened or closed to the extent necessary to obtain the desired pressure.

If complete access to the operation chamber 35 is desired the blower 21 is shut off and the curtain 60 is detached along the thistle cloth strip 71 from bar 15, the fasteners 65 moved to the top and the curtain 60 folded up on top of the enclosure 10. If desired the floor bar 64 can then be removed by taking out bolts 70 so that the enclosure can be slid into enclosing relation to animal cages or plant support racks.

The enclosure 10 can be transported by moving it on the castors 75 to the desired location for use, the castors 75 then being removed and then the gasket 51 will seal the bottom of the enclosure 10 against the floor (not shown) so that the unit is ready for use.

It will thus be seen that apparatus has been provided with which the objects of the invention are attained.

We claim:

1. A portable self contained enclosure to provide a clean room environment which comprises
a portable housing having
a frame with rigid side and rear panels,
members for detachably securing one of said side panels to one end of said frame for interior access,
said housing having an open bottom,
an air blower,
a dividing panel positioned inside said housing separating the interior of said housing into a chamber for said air blower accessible at said one of said side panels and an operational chamber,
a front wall closing said air blower chamber,
a plenum chamber attached to and closing off the top of said housing and being in communication with said air blower chamber for delivery of air thereto from said air blower chamber,
said air blower chamber being in communication with said operational chamber for receiving air therefrom,
a perforated ceiling panel member between said operational chamber and said plenum chamber,
filter means in said air blower chamber for receiving air from said air blower,
an impervious access curtain providing a front wall closing the front of said operational chamber and having members detachably securing said curtain to said frame, and
said frame having around the lower margin thereof a sealing gasket for engagement with the floor.

2. An enclosure as defined in claim 1 in which said rear wall has a clear window.

3. An enclosure as defined in claim 1 in which said access curtain has a clear window.

4. An enclosure as defined in claim 3 in which said access curtain window has along at least one edge a double slider separable fastener.

5. An enclosure as defined in claim 4 in which said access curtain is provided with an additional double slider separable fastener extending transversely across said curtain and below said window.

6. An enclosure as defined in claim 1 in which said access curtain has a portion detachably secured to said frame by at least one of said detachably securing members extending vertically along said curtain.

7. An enclosure as defined in claim 1 in which said plenum chamber is made of synthetic plastic sheet material.

8. An enclosure as defined in claim 1 in which heat exchange means for said air is provided in said air blower chamber in series with said blower.

9. An enclosure as defined in claim 1 in which the lower margin of said curtain is detachably secured to a portion of said frame.

10. An enclosure as defined in claim 1 in which means is provided for controlling the pressure within said operational chamber comprising
an air inlet connection to said air blower chamber from outside the housing and communicating with the inlet of said blower, and
members at said air inlet connection for controlling the access of air through said air inlet connection.

11. An enclosure as defined in claim 1 in which means is provided for controlling the pressure within said operational chamber comprising
an air outlet connection from said air blower chamber to the outside of said housing and communicating with the outlet of said blower, and members at said air outlet connection for controlling discharge of air through said air outlet connection.

12. An enclosure as defined in claim 1 in which means is provided for controlling the pressure within said chamber comprising an air inlet connection to said air blower chamber from outside the housing and communicating with the inlet of the blower, members at said air inlet connection for controlling the access of air through said air inlet connection, an air outlet connection from said air blower chamber to the outside of said housing and communicating with the outlet of said blower, and members at said air outlet connection for controlling the discharge of air through said air outlet connection.

* * * * *